United States Patent [19]
Klemm et al.

[11] 3,944,667
[45] Mar. 16, 1976

[54] FORMYLAZAPENTADIENENITRILES

[75] Inventors: Kurt Klemm, Allensbach; Erhard Langenscheid, Constance, both of Germany

[73] Assignee: Byk Gulden Lomberg Chemische Fabrik GmbH, Constance, Germany

[22] Filed: Sept. 4, 1973

[21] Appl. No.: 393,811

[30] Foreign Application Priority Data
Sept. 8, 1972  Luxemburg............................ 66036
Sept. 8, 1972  Luxemburg............................ 66037
Sept. 8, 1972  Luxemburg............................ 66038

[52] U.S. Cl. ......... 424/244; 260/239 E; 260/239 A; 260/293.87; 260/326.5 J; 260/464; 260/465.5 R; 424/267; 424/274; 424/304
[51] Int. Cl.² ............... C07C 121/34; A61L 13/00; A01N 9/22; C07C 121/48
[58] Field of Search ..... 260/465.5 R, 239 E, 239 A, 260/326.5 J, 293.87, 464; 424/304, 244, 274, 267

[56] References Cited
UNITED STATES PATENTS

| | | |
|---|---|---|
| 2,532,561 | 12/1950 | Langkammerer.......... 260/293.87 X |
| 3,057,864 | 10/1962 | Shulgin........................ 260/239 E X |
| 3,277,103 | 10/1966 | Trofimenko .............. 260/326.5 J X |
| 3,523,119 | 8/1970 | Jutz et al..................... 260/465.5 R |
| 3,542,848 | 11/1970 | Leimgruber et al. ..... 260/465.5 R X |
| 3,655,665 | 4/1972 | Meindl et al..................... 260/465.4 |
| 3,792,076 | 2/1974 | Leimgruber et al. .... 260/465.5 R X |
| 3,873,596 | 3/1975 | Klemm et al................. 260/465.5 R |

*Primary Examiner*—Joseph P. Brust
*Attorney, Agent, or Firm*—Berman, Aisenberg & Platt

[57] ABSTRACT

Insecticidal, fungicidal and bactericidal substituted formylazapentadienenitriles are prepared by hydrolyzing an azapentadienylidene ammonium salt of the formula

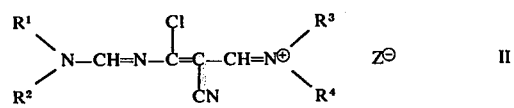

II

5 Claims, No Drawings

FORMYLAZAPENTADIENENITRILES

RELATED APPLICATIONS

This application is related to three concurrently-filed applications of the subject inventors. These applications are entitled 3-CHLORO-2-HYDRAZONOMETHYL-4-AZA-2,4-PENTADIENENITRILES, Ser. No. 393,812, now abandoned; 2-HYDRAZONOMETHYL-3-HYDROXY-4-AZA-2,4-PENTADIENENITRILES, Ser. No. 393,813; and 4(1H)-PYRIMIDINONES, Ser. No. 393,814. The disclosure of each of the related applications is incorporated herein by reference.

BACKGROUND

In the reaction of N-(3-chloro-4-cyano-5-dimethylamino-2-aza-2,4-pentadienylidene)-N,N-dimethylammonium perchlorate with nucleophilic reagents, substitution of the chlorine atom occurs [Ch. Jutz and W. Muller, Angew. Chem., 78, 1059 (1966)]. Thus, with an aqueous ammonia or ammonium chloride solution 4-dimethylamino-5-pyrimidinylcarbonitrile is produced with a splitting off of the two dimethylamino groups and simultaneous substitution of the chlorine atom.

SUMMARY

4-Aza-3-chloro-2-formyl-5-(tertiary)amino or cycloimino-2,4-pentadienenitriles of the formula

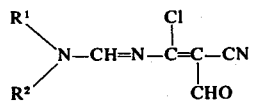

wherein
  $R^1$ is alkyl having from 1 to 7, preferably from 1 to 4, carbon atoms, cycloalkyl having from 3 to 6 ring carbon atoms or, together with $R^2$ and the nitrogen atom to which both are bound, a heterocyclic ring containing at least 2 ring carbon atoms and having from 3 to 6 ring members, ordinarily with at least two of the ring members being carbon atoms and at least one ring member being —O—, —S— or —N($R^7$)—;
  $R^2$ is alkyl having from 1 to 7, preferably from 1 to 4, carbon atoms, cycloalkyl having from 3 to 6 ring carbon atoms or, together with $R^1$ and the nitrogen atom to which both are bound, a heterocyclic ring having from 3 to 6 ring members, ordinarily with at least two of the ring members being carbon atoms and at least one ring member being -O-, —S— or —N($R^7$)—; and
  $R^7$ is a hydrogen atom (—H) or alkyl having from 1 to 7, preferably from 1 to 4, carbon atoms;
and their salts with organic or inorganic acids are useful as insecticides, for destroying or retarding the growth or proliferation of microorganisms, as fungicides and bactericides, as well as for intermediates for the synthesis of pharmaceuticals. They are prepared by hydrolyzing (preferably in admixture with organic solvent which is miscible with water) an azapentadienylidene ammonium salt of the formula

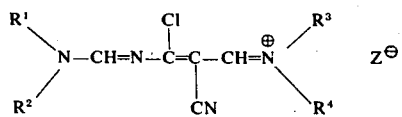

wherein each of
  $R^1$ and $R^2$ has its previously-ascribed meaning; each of $R^3$ and $R^4$ has one of the meanings of $R^1$ and $R^2$, respectively; and
  $Z^-$ is an equivalent of an anion of an organic or inorganic acid; and, if desired, converting any thus-obtained free base into an acid addition salt or converting any thus-obtained acid addition salt into another such salt or into the corresponding free base.

In compounds of formula II $Z^-$ is preferably an equivalent of an anion of a strong inorganic or organic acid and, for process reasons, particularly of such an anion which forms (with the cation of formula II) a salt which is sparingly soluble in water, for example an equivalent of an anion of picric, styphnic, picrolonic, hexachloroplatinic, hydriodic or tetrafluoroboric acid and primarily a perchlorate.

DETAILS

The starting materials of formula II are conventional or are produced in a conventional manner from available materials, e.g. malonic dinitrile, cyanoacetic ester or cyanoacetamide, by Vilsmeyer formylation (Cf. Belgian patent specification 739,243).

Throughout the disclosure each reference to alkyl includes both straight chain and branched chain alkyl, e.g. methyl, ethyl, propyl, isopropyl, butyl, isobutyl, sec.-butyl or tert.-butyl, pentyl, isopentyl, 1- or 2-methylbutyl, tert.-pentyl, hexyl, isohexyl, 1-, 2- or 3-methylpentyl, 1-, 2- or 3-ethylbutyl, 1,2- 1,3- or 2,3-dimethylbutyl, heptyl or isoheptyl, unless otherwise limited. In each of $R^1$ to $R^4$ each alkyl has from 1 to 7, preferably from 1 to 4, carbon atoms.

Each cycloalkyl has from 3 to 6 ring carbon atoms and is, for example, a cyclopropyl, cyclopentyl, 2- or 3-methylcyclopentyl or, preferably, a cyclohexyl group.

An alkylene group made up of the radicals $R^1$ and $R^2$ (or $R^3$ and $R^4$) has from 2 to 5 carbon atoms and is straight chained or branch chained, for example, an ethylene, trimethylene, 1- or 2-methylethylene, tetramethylene, 1-, 2- or 3-methyltrimethylene, 1- or 2-ethylethylene or, preferably, a pentamethylene group.

When each of one or more ring carbon atoms of such an alkylene group is replaced by a hetero atom, the resulting composite of $R^1$ and $R^2$ (or $R^3$ and $R^4$) is, e.g. 3-aza-, 3-thia- or, preferably, 3-oxa-pentamethylene.

Preferred compounds are those of the formula

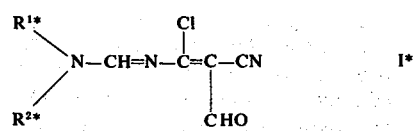

wherein each of $R^{1*}$ and $R^{2*}$ is, independently, an alkyl with from 1 to 4 carbon atoms, particularly 3-chloro-5-dimethylamino-2-formyl-4-aza-2,4-pentadienenitrile.

In addition to their insecticidal, bactericidal and fungicidal utility, such compounds are particularly valuable as pharmaceutical intermediates.

Compounds of formula I are employed as pharmaceutical intermediates according to the following reaction schemes:

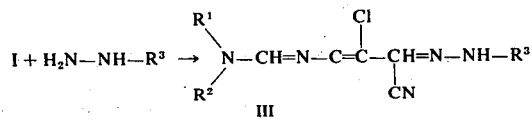

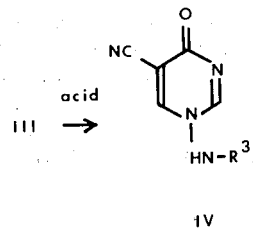

wherein

R$^3$ is an acyl radical of an organic acid, such as carbonic acid or a carboxylic acid, or a functional derivative thereof and preferably one of the following radicals:

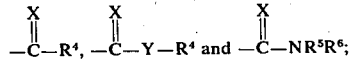

R$^4$ is a hydrogen atom (—H), an alkyl with from 1 to 14 carbon atoms, cycloalkyl with from 3 to 6 carbon atoms, substitued or unsubstituted phenyl or phenalkyl;

each of R$^5$ and R$^6$ is, independently, a hydrogen atom (—H), alkyl, cycloalkyl or together denote an alkylene group with from 2 to 5 carbon atoms;

X is =S, =O or =NR$^7$;

Y is -S- or -O-;

R$^7$ is a hydrogen atom (-H) or alkyl; and each of R$^1$ and R$^2$ has its previously-ascribed meaning.

Compounds of formulae III and IV and their pharmacologically-acceptable salts are useful for treating gout and, as such, are orally administrable in conventional dosage forms.

The compounds of formula I and their salts with organic and inorganic acids are thus valuable chemical intermediate products for the production of pharmacologically active compounds, for example substituted 5-amino-3-chloro-2-hydrazonomethyl-4-aza-2,4-pentadieneitriles, such as are described in the previously-noted application Ser. No. 393,812. In view of their structure as β-halogen vinylaldehydes, reaction thereof with substituted or non-substituted hydroxylamines, hydrazines, semicarbazides, amidines, guanidines or aminovinyl esters yields heterocyclics of the oxazol, pyrazol, pyridine and pyrimidine series (optionally containing still further functional groups), which are important as dyes, for plant protection and, more particularly, as pharmaceutical chemicals.

According to the subject invention an azapentadienylidene ammonium salt of formula II is reacted with water to form a corresponding formylazapentadienenitrile of formula I and/or a salt thereof with an organic or inorganic acid.

Compounds of formula I are thus obtained (according to reaction conditions) in free base form or in the form of an acid addition salt. These forms are interconverted in conventional manner.

The hydrolysis is preferably carried out in an aqueous organic medium, i.e. in the presence of or in admixture with organic solvents which are soluble in water or miscible with water, while cooling, at room or at an elevated temperature, preferably at from —20° to +50°C, and in particular at from 20° to 30°C. The operation is preferably carried out in the presence of a suitable stabilizer, preferably in the presence of pyrogallol. The ratio of water to organic solvent is variable within wide limits, the operation being carried out conveniently with a ratio of 1:10 to 10:1. Organic solvents in the aqueous organic reaction medium are soluble in water or solvents which can be mixed with water, for example alcohols, such as methanol, isopropanol and butanol; glycols, such as triethyleneglycol and 1,2-propanediol, dioxane; glycolethers, such as diethyleneglycoldimethylether; ketones, for example acetone and methylethylketone; formamide; dimethylformamide and dimethylsulfone, of which one or more can be used together with water, and more particularly ethanol or acetonitrile.

The conditions in the above-described reaction are selected to take into account all substituents in the starting compound of formula II.

Insecticidal, fungicidal and bactericidal compositions contain one or more of the compounds of the general formula I or its salts with organic or inorganic acids, preferably 3-chloro-5-dimethylamino-2-formyl-4-aza-2,4-pentadienenitrile, in a concentration of 10 to 10,000 parts per million, preferably 100 to 1,000 parts per million and usual carriers therefor. The compositions are solid, such as a powder, or liquid, such as a suspension, emulsion or solution. Useful carriers for powders are, for example, China clay, starch, talcum, calcium phosphate and solid high molecular polymers. Carriers for suspensions, emulsions and solutions are solvents, e.g. water, organic solvents, such as paraffins, plant oils and glycols, and nonionic or anionic emulsifiers, such as polyoxyethylene fatty acids and alkyl- or arylsulfonates, and dispersing agents, such as lignin. The carriers are used in conventional proportions. If the compositions are to be diluted prior to actual use, the concentration of the active ingredient is correspondingly higher.

The compounds of formula I are valuable bactericides and fungicides: For example 3-chloro-5-dimethylamino-2-formyl-4-aza-2,4-pentadienenitrile stops the growing of gram positive bacteria in a minimal concentration of 80 γ/ml (Staph.aur., Strepto Gr.B, C, Entero) or 500γ/ml (Strepto Gr.A) of nutrient broth (glucose) and stops the growing of yeast in a minimal concentration of 500γ/ml (C. albicans) or 125 γ/ml (C. paracrusei) of nutrient broth (Sabouraud solution) and acts against the proliferation of trichomonads in a minimal concentration of 250 γ/ml of nutrient broth (Bacto fluid thioglycollate medium with addition of 10 % bovin serum).

Without further elaboration, one skilled in the art can, using the preceding description, utilize the present invention. The following specific embodiments are merely illustrative and not limitative of the remainder of the disclosure or of the invention described therein in any way whatsoever.

EXAMPLE 1

100 g of N-(3-chloro-4-cyano-5-dimethylamino-2-aza-2,4-pentadienylidene)N,N-dimethylammonium perchlorate are dissolved in a mixture of 400 ml of acetonitrile and 400 ml of water. Stirring is carried out for 6 hours at 20° to 22°C and is followed by double extraction with two 400 ml portions of trichloromethane. Following this the combined trichloromethane phases are extracted twice with two 1000 ml portions of water. The organic phase is dried with $Na_2SO_4$ or $MgSO_4$ and reduced in volume by distilling off of the solvent at 30° to 35°C to a quarter of the original volume. After allowing the resultant to stand for one hour in an ice-box at about 0°C, the precipitate is vacuum filtered to yield yellowish crystals. 36 g (61%) of 3-chloro-5-dimethylamino-2-formyl-4-aza-2,4-pentadienenitrile, with a melting point of 144°C (with decomposition), are thus obtained.

Replacing the N-(3-chloro-4-cyano-5-dimethylamino-2-aza-2,4-pentadienylidene)-N,N-dimethylammonium perchlorate with an equivalent of N-(3-chloro-4-cyano-5-diethyl-, diisopropyl- or ethylmethylamino-2-aza-2,4-pentadienylidene)-N,N-dimethylammonium perchlorate results in the preparation, in similar manner, of the corresponding formylazapentadienenitrile of formula I.

EXAMPLE 2

31.4 g of N-(3-chloro-4-cyano-5-dimethylamino-2-aza-2,4-pentadienylidene)-N,N-dimethyl ammonium perchlorate and 0.1 g of pyrogallol are stirred in a mixture of 140 ml of water and 200 ml of ethanol for one hour at 25° to 30°C. Precipitaion of reaction products is completed by addition of 500 g of ice. Vacuum filtration is then carried out. This is followed by washing with cold water. Drying is effected at 20°C over $P_2O_5$. 13.2 g (71.2%) of 3-chloro-5-dimethylamino-2-formyl-4-aza-2,4-pentadienenitrile, with a melting point of 145° to 147°C (with decomposition), are thus obtained in the form of pale needles.

Replacing the N-(3-chloro-4-cyano-5-dimethylamino-2-aza-2,4-pentadienylidene)-N,N-dimethylammonium perchlorate with an equivalent of N-(3-chloro-4-cyano-5-(aziridin-1-yl)-, pyrrolidin-1-yl-piperidino-, morpholino-, piperazin-1-yl pyrozolidin-1-yl-2-aza-2,4-pentadienylidene)-N,N-dimethylammonium perchlorate results in the preparation, in similar manner, of the corresponding formylazapentadienenitrile of formula I.

The preceding description of the present invention is susceptible to various modifications, changes and adaptations, as is readily apparent to those skilled in the subject art.

What is claimed is:

1. A compound of the formula

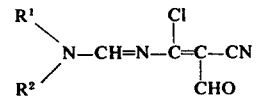

wherein
$R^1$ is alkyl with from 1 to 7 carbon atoms, cycloalkyl with from 3 to 6 ring carbon atoms or, together with $R^2$, alkylene with from 2 to 5 carbon atoms;
$R^2$ is alkyl with from 1 to 7 carbon atoms, cycloalkyl with from 3 to 6 ring carbon atoms or, together with $R^1$, alkylene with from 2 to 5 carbon atoms;
in free base or acid addition salt form.

2. A compound according to claim 1 wherein each of $R^1$ and $R^2$, independently, has from 1 to 4 carbon atoms.

3. A compound of claim 2 which is 3-chloro-5-dimethylamino-2-formyl-4-aza-2,4-pentadienenitrile.

4. A microbiocidal composition consisting essentially of active ingredient and carrier, a microbiocidally-active ingredient of which is a compound according to claim 1.

5. An insecticidal composition consisting essentially of active ingredient and carrier, the composition containing an insecticidally-effective concentration of an insecticidally-active compound according to claim 1.

* * * * *